United States Patent [19]

Hata

[11] 4,345,032

[45] Aug. 17, 1982

[54] CULTIVATION OF A DEODORIZING LACTOBACILLUS STRAIN, STORAGE THEREOF, AND COMPOSITION CONTAINING LIVING CELLS THEREOF

[75] Inventor: Kosei Hata, Osaka, Japan

[73] Assignee: Seikenkai, Osaka, Japan

[21] Appl. No.: 799,320

[22] Filed: May 23, 1977

[51] Int. Cl.$^3$ .................. C12N 1/20; C12N 1/04; C12R 1/225; A61K 37/00

[52] U.S. Cl. .................. 435/253; 435/245; 435/760; 435/853; 71/6; 71/8; 71/9; 71/10; 210/601; 424/93

[58] Field of Search .................. 195/96, 52, 76, 79; 424/93, 76; 426/71; 71/8, 9, 10, 6; 210/2, 601; 435/244, 245, 253, 260, 853, 172

[56] References Cited

U.S. PATENT DOCUMENTS

| | | | |
|---|---|---|---|
| 2,703,302 | 3/1955 | Rickes et al. | 195/96 X |
| 3,227,648 | 1/1966 | Hahn et al. | 210/2 |
| 3,953,609 | 4/1976 | Farr | 424/93 X |
| 3,957,974 | 5/1976 | Hata | 424/93 |

FOREIGN PATENT DOCUMENTS

| | | | |
|---|---|---|---|
| 45-22516 | 7/1970 | Japan | 195/79 |
| 930107 | 7/1963 | United Kingdom | 424/93 |

OTHER PUBLICATIONS

Mitic, "Transformation of Amino Acid Composition in Bacterial Cells of *Lactobacillus bulgaricus* During Freeze-Drying", *Chem. Abstracts*, vol. 85, No. 3, (1976), p. 333, Abs. #17012h.

Holden et al., "Stimulation by Fatty Acids of Amino Acid Accumulation in Pantothenic Acid Depleted *Lactobacillus plantarum*", *Biochem. and Biophys. Res. Comm.*, vol. 46, No. 2, (1972), pp. 437–442.

Fontanges, "Etude de l'Influence de Plusienes Parametres dans la Conservation par Lyophilization de *Yersihia pestis*, (Souche EV)", *Freeze Drying and Advanced Food Technology*, Goldblith et al., Academic Press, (1973), N.Y., pp. 95, 96.

Benedict et al., "Preservation of Microorganisms by Freeze-Drying", *App. Microbiol.*, vol. 6, No. 6, (1958), pp. 401–407.

*Primary Examiner*—Thomas G. Wiseman
*Attorney, Agent, or Firm*—Sughrue, Mion, Zinn, Macpeak & Seas

[57] ABSTRACT

The present invention relates to deodorization of excrement by Lactobacillus strains in cultivation of said strains with S-, N- or C-compounds which are odoriferous components of said excrement and/or certain amino acids.

13 Claims, 9 Drawing Figures

CULTIVATION OF A DEODORIZING LACTOBACILLUS STRAIN, STORAGE THEREOF, AND COMPOSITION CONTAINING LIVING CELLS THEREOF

BRIEF SUMMARY OF THE INVENTION

This invention relates to a method of cultivating novel Lactobacillus strains of special character which have been first found and isolated by the inventor. This invention also relates to a method of preserving said living Lactobacillus strains without losing their activity and to deodorant compositions containing them as an active ingredient thereof.

BRIEF DESCRIPTION OF THE DRAWINGS

FIG. 4 shows the results which were determined by adding acetic acid to (S-W)+vitamins+casamino acids, and the results of FIGS. 5 and 6 were determined by adding $Na_2S$ and $NH_3$ thereto, respectively. FIG. 7 shows the results which were determined in a low nutritional medium containing acetic acid, and, in FIGS. 8 and 9, $Na_2S$ and $NH_3$ were employed instead of said acetic acid. (1) shows the growth rate of the Lactobacillus of the present invention in a medium containing an additive, and (1') that of the known Lactobacillus in the same medium. On the other hand, (2) and (2') show the result of control tests for the Lactobacillus of the present invention and the known Lactobacillus, respectively. Said control tests were carried out in a medium not containing the additive.

DETAILED DESCRIPTION OF THE INVENTION

Figure 1:
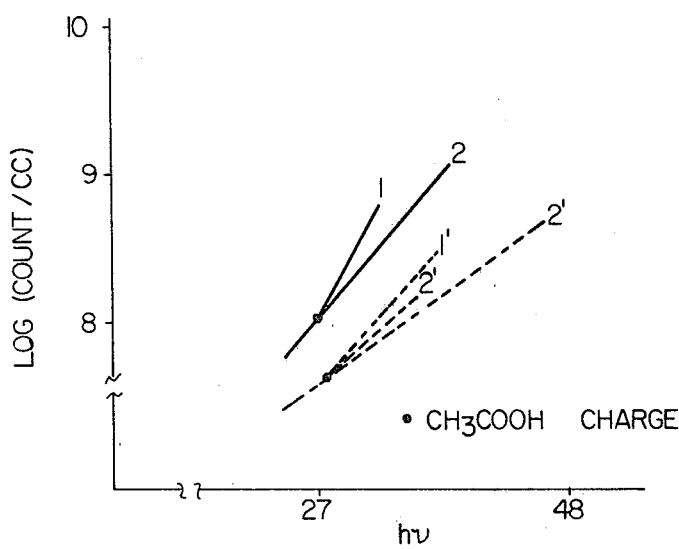
FIGS. 1 through 9 show the growth rate of the Lactobacillus of the present invention and the known Lactobacillus in their log phase. The results of FIG. 1 were determined in LC medium (basic medium) containing acetic acid. The results of FIG. 2 were determined in said basic medium containing $Na_2S$, and those of FIG. 3 in said basic medium containing $NH_3$.

Specific Lactobacillus strains which have the ability to deodorize foul odor from human or livestock excrement, foul breath and vaginal odor have been reported in Japanese patent applications have been filed for some of them (Japanese patent application No. 134773/1974 and U.S. 3957974. Now, various investigations have been continued with respect to Lactobacillus strains including those found by the inventor, and at the same time, the deodorizing activity of these strains and the relation thereof to their microbiological properties have been further scrutinized. The present invention has been established based on these investigations.

Firstly, the present inventor has now succeeded in separating many Lactobacillus strains having a high deodorizing activity. Said strains exhibit excellent deodorizing activity even when administered orally to humans and livestock or when applied directly to their excrements. Secondly, after having studied the properties of these strains, the inventor has succeeded in ascertaining the relationship between the deodorizing activity of said strains and the microbiological properties thereof. Simultaneously, it has been made clear that, with respect to the Lactobacillus strains having the deodorizing activity, the conditions for cultivation, subculture and preservation thereof must be quite different from those employed for known strains. The results of experiments carried out by the inventor with respect to the deodorizing Lactobacillus strains are shown in the following lines. That is, the Lactobacillus strains which can be recognized organoleptically to have deodorizing activity must have the following characteristic properties.

As essential properties, they must
(1) be resistant to bile
(2) have lower nutritional requirements as compared with known Lactobacillus strains
(3) show high growth rate even in a medium containing poor nutrients and
(4), in a single or plural strains, satisfy the S.N. C-theory found by the inventor and explained in detail hereinafter.

As important properties for exhibit deodorizing activity effectively, they must
(5) have sufficient productivity of antibiotics and lactic acid and
(6) be resistant to antibacterial compounds including condiments.

Before explaining in detail the above-mentioned properties, the microbiological properties of known Lactobacillus must be explained in connection with the present invention. According to Dr. Mitsuoka, the morphology of Lactobacillus has been defined as follows:

Gram-negative, facultative anaerobic, non-spore forming rods. Depending on the strains they may be spherical rod-like, curved rod-like, coryne-like or thread-like, but do not form so many branches. They are usually non-motile, negative to catalase and do not reduce nitrates. They do not decompose gelatin and do not produce indole or hydrogen sulfide. Some of the strains are bipolar-stained. Their ability to decompose protein and fat is very weak, if any. They show better growth under anaerobic or microaerophilic conditions rather than under aerobic conditions, have strong ability to decompose sugars, and are acid-fast. When used for glucose fermentation, they produce lactic acid in an yield of more than 50%. They are not pathogenic to animals and plants.

Moreover, it is known that the Lactobacillus strains having these properties defined above can grow only in media containing good nutrients such as amino acids, peptides, nucleic acid analogs, vitamins, salts, fatty acids or their esters and sugars.

The Lactobacillus strains which have been recognized by the inventor as having the deodorizing activity show the same morphological characteristics as those of known Lactobacillus strains, but are quite different from the latter in the properties (1), (2) and (3) mentioned hereinbefore.

The important points among the above are explained in details in the following lines.

(A) As mentioned above, the known Lactobacillus strains require amino acids, peptides, nucleic acid analogs, vitamins, salts, fatty acids or their esters and sugars for their growth, and they have been known to belong to a group of bacteria which have relatively high nutritional requirements. Therefore, good nutritional media such as Briggs' and MRS media must have been generally used for cultivation of the Lactobacillus strains.

(B) The Lactobacillus strains which have been found by the inventor and are used in the present invention (hereinafter simply referred to as "the Lactobacillus of the invention", unless otherwise indicated) show quite different characteristics as compared with the known Lactobacillus. That is, the Lactobacillus of the invention not only exhibits good growth in good nutritional media such as Briggs' medium, but, as shown in Table 1, it also grows well in media containing poor nutrients only.

TABLE 1

| Strains (FERM-P Nos.) | Media used | | | | |
|---|---|---|---|---|---|
| | Briggs | LC | (S-W) + casamino acids + viamins | (S-W) + vitamins | (S-W) + casamino acids |
| Lactobacillus strain commercially available; | ++ | +++ | − | − | |
| 1946 | +++ | +++ | ++ | + | ++ |
| 2742 | +++ | +++ | ++ | + | ++ |
| 2779 | +++ | +++ | ++ | − | + |
| 2780 | +++ | +++ | ++ | − | + |
| 2781 | +++ | +++ | ++ | − | + |
| 2782 | +++ | +++ | ++ | − | + |

(C) As shown in Table 2, the Lactobacillus of the invention when cultivated in Briggs' and MRS media is apparently superior to the known Lactobacillus in the growth rate and final number of cells thereof.

TABLE 2

| Strains (FERM-P Nos.) | Media | | | |
|---|---|---|---|---|
| | MRS | | Briggs | |
| | Specific growth rate($\mu$) | Final number of cells(cc) | Specific growth rate($\mu$) | Final number of cells(cc) |
| 1946 | 0.516 | 65 × 10$^8$ | 0.53 | 40 × 10$^8$ |
| 2742 | 0.597 | 80 × 10$^8$ | 0.57 | 50 × 10$^8$ |
| 2779 | 0.53 | 60 × 10$^8$ | 0.51 | 35 × 10$^8$ |
| 2780 | 0.47 | 70 × 10$^8$ | 0.45 | 40 × 10$^8$ |
| 2781 | 0.53 | 70 × 10$^8$ | 0.51 | 40 × 10$^8$ |
| 2782 | 0.47 | 60 × 10$^8$ | 0.45 | 35 × 10$^8$ |
| Mean value for known lactobacillus | 0.40 | 20 × 10$^8$ | 0.38 | 15 × 10$^8$ |

(D) Further, as seen from the above-mentioned nutritional requirements, S-W medium (a), (S-W+vitamins)-medium (b) and even (S-W+casamino acids)medium (c) are unsuitable for growth of the known Lactobacillus. With respect to this point, the result of experiments carried out by the inventor are shown in Table 4.

(E) On the contrary, the Lactobacillus of the invention can in almost all cases grow in at least either one of the media (a), (b) and (c), and at the same time shows good growth rate and good final yield (number of cells/cc) therein. Concomitantly, a deodorizing Lactobacillus of the invention which grows in (S-W+vitamins+amino acids)medium but not in the above-mentioned media (a), (b) and (c) has been further found by the inventor.

Each one of the LC and (S-W)media described above is shown as follows. LC medium: 10 g of peptone, 10 g of meat extracts, 5 g of NaCl, 3 g of K$_2$HPO$_4$, 10 g of glucose, 5 g of yeast extracts, 3 g of CaCO$_3$ and 10 liters of water, pH 7.4 (S-W) medium: 1 g of KH$_2$PO$_4$, 0.7 g of MgSO$_4$ 7H$_2$O, 1 g of NaCl, 4 g of (NH$_4$)$_2$HPO$_4$, 0.03 g of FeSO$_4$ 7H$_2$O, 5 g of glucose and 1 liter of water. Briggs' medium: Briggs. M. (1953) can be prepared according to "An Improved Medium For Lactobacilli" described in J. Dairy Res. 20, 36. MRS medium: DEMAN J. C., ROGOSA M & SHARPE. M. E.(1960) is prepared according to J. Appl. Bact. 23(1), 130–135.

The facts shown in the above-mentioned paragraphs (D) and (E) are summarized in the following Tables 3-1 and 3-2.

TABLE 3-1

| Strains | Media |
|---|---|
| | Either one of (a), (b) and (c) |
| Lactobacillus of the invention | + |
| Known Lactobacillus | − |

TABLE 3-2

| $\mu$ and Yield (number of cells/cc) | | |
|---|---|---|
| Lactobacillus of the invention (Medium used: (c)-medium) | ≈ | Known Lactobacillus (Medium used: Briggs' medium) |

As is clear from the above, the Lactobacillus of the invention when cultivated in a low nutritional medium such as the medium (c) shows almost the same growth rate and yield as those of the known strains cultivated in a good nutritional medium such as Briggs' medium. At any rate, the particulars of the test results as to the six representative Lactobacillus strains of the invention, each of which have different nutritional requirements, are shown as follows:

TABLE 4

| Strains (FERM-P Nos.) | Test items | Media | | |
|---|---|---|---|---|
| | | (a) | (b) | (c) |
| 1946 | Growth | − | + | ++ |
| | $\mu$ | | 0.17 | 0.53 |
| | Yield | | 5 × 10$^8$ | 25 × 10$^8$ |
| 2742 | Growth | + | + | ++ |
| | $\mu$ | 0.20 | 0.40 | 0.56 |
| | Yield | 7 × 10$^8$ | 20 × 10$^8$ | 50 × 10$^8$ |
| 2779 | Growth | − | − | + |
| | $\mu$ | | | 0.35 |
| | Yield | | | 8 × 10$^8$ |
| 2780 | Growth | − | + | + |
| | $\mu$ | | 0.3 | 0.35 |
| | Yield | | 6 × 10$^8$ | 20 × 10$^8$ |
| 2781 | Growth | − | − | + |
| | $\mu$ | | | 0.53 |
| | Yield | | | 30 × 10$^8$ |
| 2782 | Growth | − | − | + |
| | $\mu$ | | | 0.35 |
| | Yield | | | 8 × 10$^8$ |

Note: Yield is shown by the number of cells/cc.

(F) It has never been reported that the known Lactobacillus might exhibit growth or growth promotion by adding one or more S,N,C-compounds to the above-mentioned media (a), (b) and (c). And in fact, as shown in Table 6, the investigations of the inventor reveal the negative results on this point.

(G) On the contrary, however, Table 6 shows that the Lactobacillus of the invention when cultivated, will grow or exhibit growth promotion in all of or at least one of the media (a), (b) and (c) which contain the S.N.C-compounds i.e. S-,N- or C-compounds.

TABLE 5

| Summary of paragraphs (F) and (G) | |
|---|---|
| | Growth or promotion of growth |
| | Compounds added to the media |
| | S.N.C—compounds were added to |
| Strains | either one of (a), (b) and (c) |
| Lactobacillus of the invention | + |
| Known Lactobacillus | − | above mentioned S,N,C—compounds mean S—, N—, or C—compounds

TABLE 6

Nutritional requirements and growth
or growth promotion of the
Lactobacillus of the invention

| Strains (FERM-P Nos.) | Basic medium | Compounds added to the basic medium | | | | | | | | | |
|---|---|---|---|---|---|---|---|---|---|---|---|
| | | i | ii | iii | iv | v | vi | vii | viii | ix | x |
| 1946 | (a) | − | + | + | + | + | + | + | + | + | + |
| | (b) | + | ++ | ++ | ++ | ++ | ++ | + | ++ | ++ | ++ |
| | (c) | ++ | ++ | ++ | ++ | ++ | ++ | ++ | ++ | ++ | ++ |
| 2742 | (a) | + | + | + | + | + | + | + | + | + | + |
| | (b) | + | ++ | ++ | ++ | ++ | ++ | ++ | ++ | ++ | ++ |
| | (c) | ++ | ++ | ++ | ++ | ++ | ++ | ++ | ++ | ++ | ++ |
| 2779 | (a) | − | − | − | − | − | − | − | − | − | − |
| | (b) | − | + | + | + | − | − | − | − | − | − |
| | (c) | + | ++ | ++ | ++ | ++ | ++ | + | ++ | ++ | + |
| 2780 | (a) | − | − | − | − | − | − | − | − | − | − |
| | (b) | + | + | + | + | + | + | + | + | + | + |
| | (c) | + | ++ | ++ | ++ | ++ | ++ | + | ++ | ++ | ++ |
| 2781 | (a) | − | + | + | + | + | + | − | + | + | + |
| | (b) | − | + | + | + | + | + | + | + | + | + |
| | (c) | + | ++ | ++ | ++ | ++ | ++ | ++ | +− | ++ | ++ |
| 2782 | (a) | − | − | − | − | − | − | − | − | − | − |
| | (b) | − | + | + | + | − | − | − | − | − | − |
| | (c) | + | ++ | ++ | ++ | ++ | ++ | + | ++ | ++ | ++ |
| Lactobacillus available in the market | (a) | − | − | − | − | − | − | − | − | − | − |
| | (b) | − | − | − | − | − | − | − | − | − | − |
| | (c) | − | − | − | − | − | − | − | − | − | − |

Note:
i: No addition ii: cystein iii: cystine iv: methionine v: $Na_2S$ vi: ammonia vii: scatole viii: acetic acid ix: butyric acid x: propionic acid
In this experiments, $Na_2S$ $9H_2O$ was employed as $Na_2S$, glacial acetic acid as acetic acid and 37% aqueous ammonia as ammonia.

The particulars of S.N.C-compounds suggested by the inventor and used herein are explained in the following lines. According to the inventor's investigations, a wide variety of foul-smelling ingredients contained in excrements are divided into the following three groups: S-compounds, N-compounds and C-compounds. Moreover, it has been found that deodorization of foul-smelling ingredients in the excrements can be satisfactorily achieved by examining the deodorizing effects upon $H_2S$ or $Na_2S$ (S-compounds), $NH_3$, indole or scatole (N-compounds) and lower fatty acids (C-compounds) because they are representative of said S.N.C-compounds, respectively. In this connection, P-compounds can be considered to be of secondary importance.

Further, it has been determined that the Lactobacillus of the invention exhibits growth or growth promotion in an appropriately selected low nutritional medium containing S.N.C-compounds, as foul-smelling ingredients. Taking all of the above into consideration, therefore, the present inventor has designated this as the S.N.C-theory concerning microorganisms and deodorization of excrements.

Then, the growth rate of the Lactobacillus of the invention is shown in FIG. 1. In this experiment LC-medium was employed as a high nutritional medium, and acetic acid or butyric acid was added thereto. In the Figure, (1) shows the growth rate of the strain of the invention in the medium containing 5 g of acetic acid (1') shows that of the known strain in the same medium as above, and (2) and (2') show respectively the growth rate of the strain of the invention and the known strain in the medium containing 0.1 to 1 g of acetic acid. As seen in FIG. 1, the strain of the invention was promoted in its growth so slowly in the log phase, that the degree of its growth promotion was quite invisible and could hardly be observed even by counting the number of its living cells, whereas the known strain showed very high growth promotion.

Figure 2:
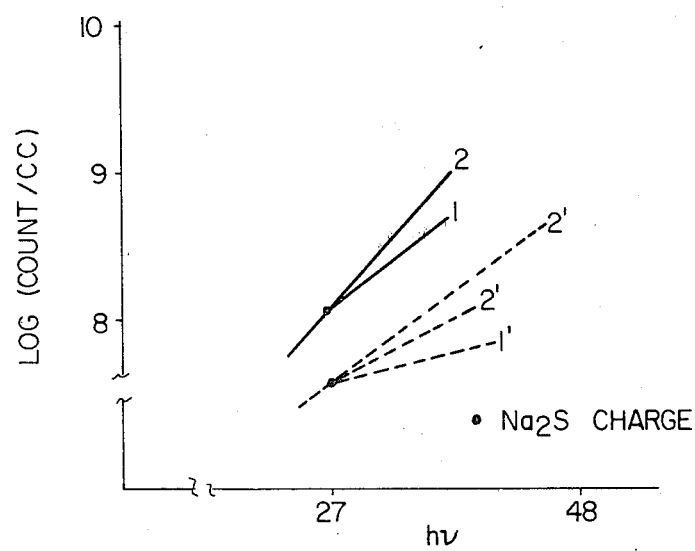
Figure 3:
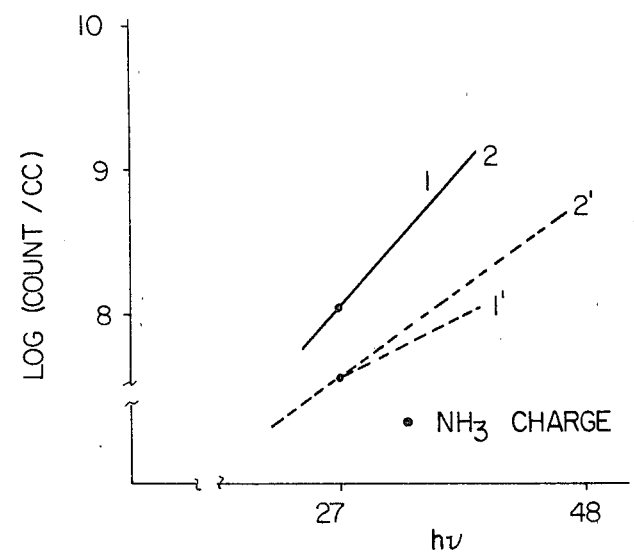

Similarly, the results which were obtained by cultivating the strains in the LC-medium containing $Na_2S$ (2 g) or $NH_3$ (2 g) are shown in FIG. 2 ($Na_2S$) and FIG. 3 ($NH_3$), respectively. The known strains exhibited inhibited growth at lower concentrations than in case of the strains of the invention, i.e., showed a higher sensibility toward the growth inhibition. 2 and 2' shows the results of control tests which were carried out in the medium containing only 0.1 g of $Na_2S$ or $NH_3$.

Figure 4:
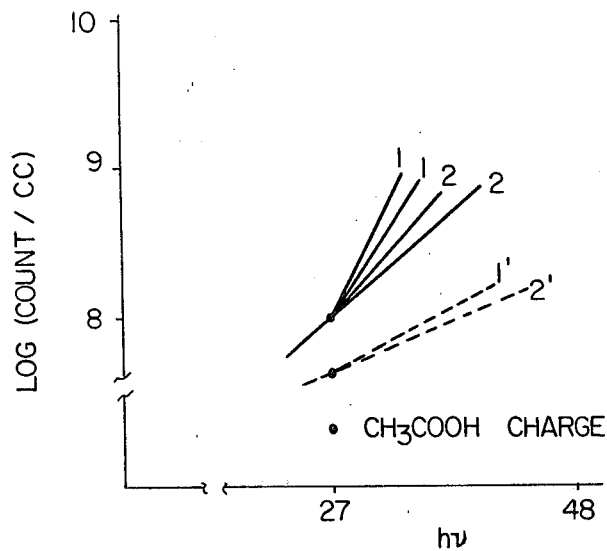
Figure 5:
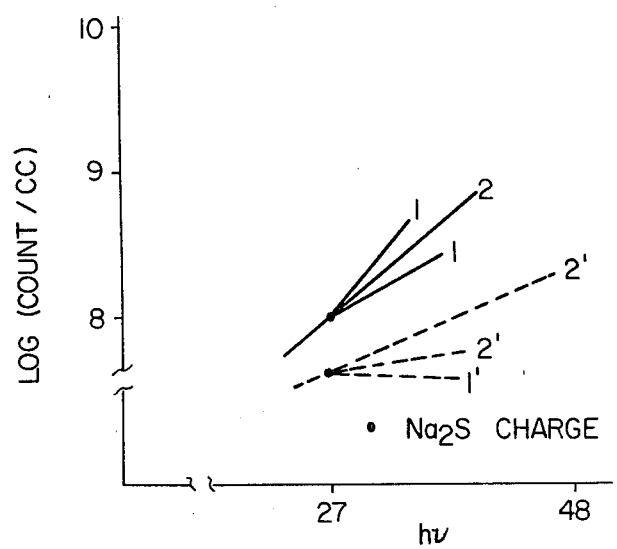
Figure 6:
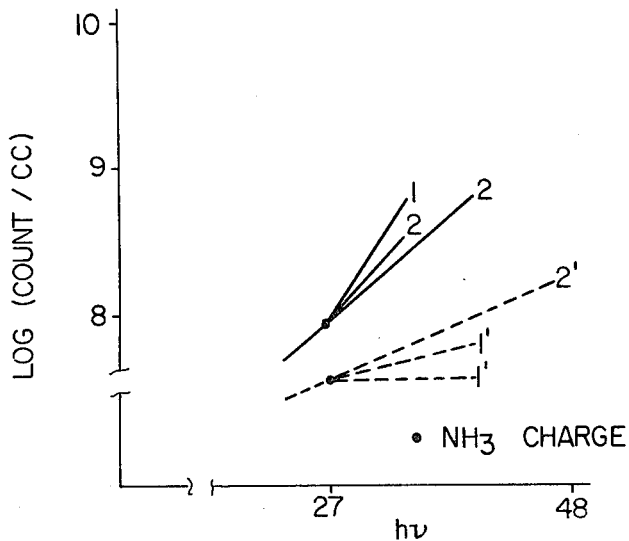

Further, the influence of S.N.C-compounds upon the growth of the Lactobacillus of the invention and the known Lactobacillus are shown in FIGS. 4 to 6. In these experiments, the strains were cultivated in high, middle and low nutritional media and, at the log phase of the strains, the S.N.C-compounds were further added thereto. As seen from the results of this experiments, addition of certain concentrations of acetic acid, $Na_2S$ and $NH_3$ to the middle nutritional medium was effective to promote the growth of the Lactobacillus of the invention, whereas the known Lactobacillus was not promoted in growth in the middle nutritional medium containing $Na_2S$ and $NH_3$.

Figure 7:
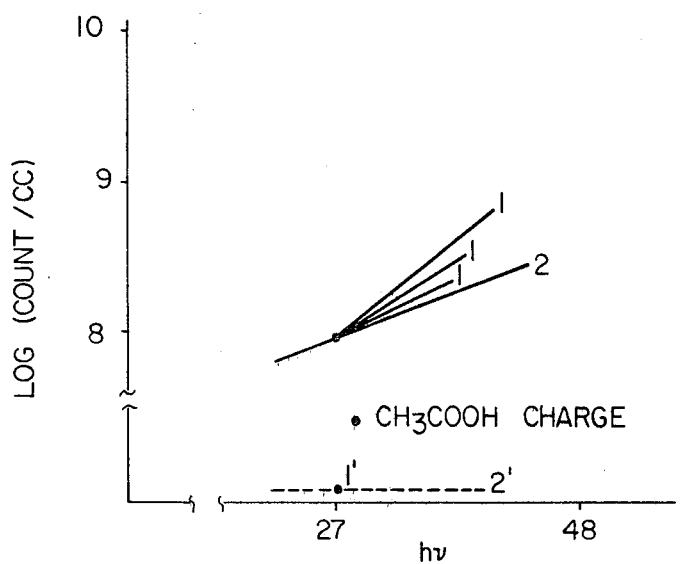
Figure 8:
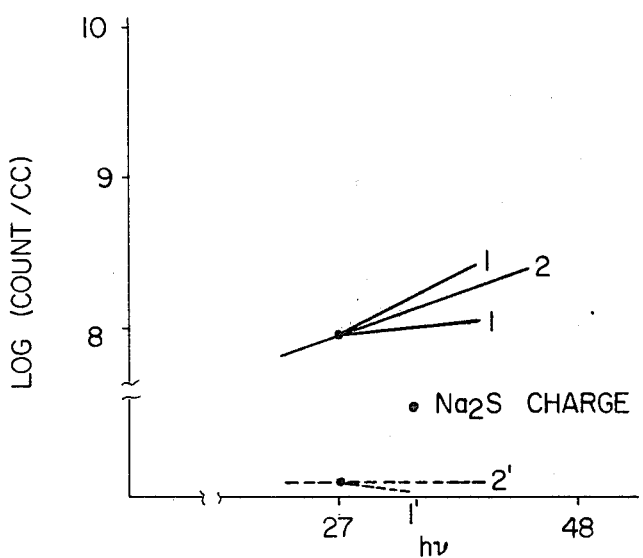
Figure 9:
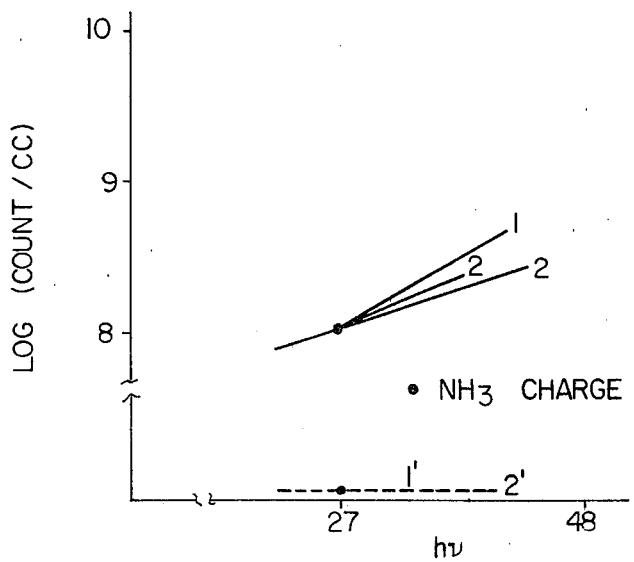

Furthermore, as shown in FIGS. 7 to 9, the known Lactobacillus does not grow in a low nutritional medium or even in said medium containing S.N-compounds. However, the lactobacillus of the invention, including the one which does not grow in (S-W)medium, will always grow in any media containing $Na_2S$. This indicates that $Na_2S$ is essential for growth of the Lactobacillus of the invention.

In FIGS. 1 through 9, the straight line (—) stands for the Lactobacillus of the invention, and the dotted line (---) the known Lactobacillus. Concomitantly, the above-mentioned relationship can be summarized as Table 7.

TABLE 7

| Conditions of experiments | | Lactobacillus Known lactobacillus | Lactobacillus of the invention |
|---|---|---|---|
| High nutritional medium | Degree of growth | ++ | +++ |
| | Compounds added: acetic acid butyric acid | ◉ | ○ |
| | Na₂S | x | x |
| | NH₃ | x | x |
| Middle nutritional medium | Degree of growth | +~− | ++ |
| | Compounds added: acetic acid butyric acid | ◉~x | ◉ |
| | Na₂S | * | ◉ |
| | NH₃ | * | ◉ |
| Low nutritional medium | Degree of growth | − | + |
| | Compounds added: acetic acid butyric acid | x | ◉ |
| | Na₂S | x | ◉ |
| | NH₃ | x | ◉ |

Note:
◉ means that the compound is essential for growth of the strain or promote the growth thereof remarkably.
⊙ means that the compound stimulates the growth of the strain fairly well.
○ means that the compound stimulates the growth of the strain slightly.
x means that the compound does not stimulate the growth of the strain.
* means that the compound inhibits the growth of the strain.

At any rate, in order that the Lactobacillus of the invention exhibit its deodorizing activity more efficiently, said Lactobacillus should preferably have the following characteristics in addition to the aforementioned ones.

(1) First of all, the lactobacillus strains should have a high productivity of antibiotics. The Lactobacillus of the present invention has been found to involve those having high, low and no productivity of antibiotics.

(2) As another preferable characteristic, the Lactobacillus should be made resistant to antibacterial compounds such as antibiotics and condiments. Namely, as suggested from the bacteriology thereof, the strains of the present invention do not show their effects sufficiently if not made resistant to the antibacterial compounds used. This fact may be seen from the result of experiments using the Lactobacillus strains of the invention as anti-inflammatory agents or deodorants, and one example of such experiments using them as the deodorants is shown in Table 8.

TABLE 8

| Tetracycline 250 ml | Effects of deodorization | |
|---|---|---|
| 4 tablets/day (p.o.) | Strain sensible to tetracycline | Strain resistant to tetracycline |
| Degree of deodorization of excrements | 3'−4 | 1 |

The Lactobacillus strain of the present invention was subcultured in the presence of tetracycline, and the resultant tetracycline-resistant strain was administered orally to men. Then, tetracycline (4 tablets per day) was further administered thereto. On the other hand, the sensible strain was employed as the control group. As seen in Table 8, the resistant strain showed its deodorizing activity as expected, whereas the sensitive strains did not almost show its effects.

(3) The other preferable characteristic is bile-resistance. Bile has strong antibacterial activity and had been used as a disinfectant in the ancient days. Therefore, the Lactobacillus strains of the invention should be resistant to bile when used for deodorization of excrements by proliferating them in intestines. Further, this fact was confirmed by the experiments which were conducted by administration of the strains to men and animals, and one example of such experiments is shown in Table 9.

TABLE 9

| Lactobacillus of the invention | Degree of deodorization (2 days after oral administration) |
|---|---|
| Strains sensible to bile | 3' |
| Strains not sensible to 25% bile powder | 1 |

As seen therein, the Lactobacillus of the present invention which was made resistant to 25% bile powder showed sufficient deodorizing activity, whereas the strains sensible to bile did not almost show said activity.

Through the inventor's investigations as to the conditions for cultivation, subculture and proliferation of the Lactobacillus strains of the invention it has been found that said strains, depending on the media employed, decrease their deodorizing activity during the subculture or proliferation thereof. In order to further investigate this phenomenon, therefore, the deodorizing activity of the strains of the invention were examined by subculturing them in high, middle or low nutritional media which optionally contain milk powder (which is known to be preferable for growth of Lactobacillus) or bile acids. In these experiments, the media which consist mainly of the aforementioned MRS or LC-medium, milk powder or a mixture thereof were employed as the high nutritional media. The medium which was obtained by adding 0.5 g of Na₂S, 0.5 g of skatole and one g of butyric acid (ingredients of excrements)(hereinafter referred to as "F-ingredients) to either one of said MRS or LC-medium, milk powder or a mixture thereof was also employed as one of the high nutritional media. On the other hand, the middle nutritional media employed consist mainly of (S-W)medium, casamino acids and vitamins, and F-ingredients and peptone were further added thereto. The low nutritional media are mainly a mixture of (S-W)medium, amino acids and vitamins, and a medium which was obtained by adding F-ingredients and/or milk powder to said mixture was also employed as one of the low nutritional media. Examples of compositions of these media are shown as follows:

(i) Low nutritional media: (1) (S-W)medium+1 g of casamino acids+10 g of bile powder; (2) (1)+F-ingredients; (3) (1)+30 g of milk powder; (4) (3)+F-ingredients; (5) (S-W)medium+0.1 g of vitamins+10 g of bile powder; (6) (5)+F-ingredients; (7) (5)+30 g of milk powder; (8) (7)+F-ingredients.

(ii) Middle nutritional media: (9) (S-W)medium+1 g of casamino acids+1 g of yeast extracts+10 g of bile powder; (10) (9)+F-ingredients; (11) (9)+30 g of milk powder; (12) (11)+F-ingredients; (13) 2 g of peptone+0.005 g of MgSO₄ 7H₂O+0.5 g of KH₂PO₄+1 g of NaCl+1.0 g of bile powder; (14) (13)+F-ingredients; (15) 1/10 MRS-medium; (16) (15)+F-ingredients; (17) 1/3 MRS-medium; (18) (17)+F-ingredients.

(iii) High nutritional media: (19) MRS-medium; (20) (19)+F-ingredients; (21) MRS+10 g of bile powder; (22) (21)+F-ingredients; (23) MRS+30 g of milk powder; (24) (23)+F-ingredients; (25) MRS+30 g of milk powder+10 g of bile powder; (26) (25)+F- ingredients; (27) milk powder medium; (28) (27)+F-ingredients; (29) LC-medium; (30) (29)+F-ingredients; (31) LC-medium+10 g of bile powder; (32) (31)+F-ingredients.

The deodorizing activity of the strains which were examined by subculturing them for a middle period in these media are shown in the following lines.

(i) First it was observed that the deodorizing Lactobacillus strains increase their growth rate at the initial and middle state or further all over the states of their growth by adding F-ingredients to either one of the low nutritional media (Nos. 1 through 8), though the specific growth rate of the strains varied depending on the media used. Moreover, whereas the deodorizing activity of the strains did not change by subculturing them for a period in the low nutritional media not containing F-ingredients, the strains sometimes increased their deodorizing activity by repeating subculture thereof in the presence of F-ingredients.

(ii) The strains showed good growth in the high nutritional media (Nos. 19 through 32), and the effects of F-ingredients upon their growth promotion was quite invisible or could not be observed even by counting the number of their living cells. Moreover, when the strains were subcultured in the high nutritional media, they showed rapid decrease in their deodorizing activity by repeating said subculture irrespective of whether F-ingredients were added to the media. Lactobacillus strains (e.g., those employed in preparing commercial lactic beverages) which neither grow in middle nutritional media nor show any substantial deodorizing activity were inhibited in their growth by adding F-ingredients to the low and middle nutritional media, and at the same time they showed no sensibility in the high nutritional media as in case of the Lactobacillus strains of the present invention.

As is clear from the above, in order to prevent the deodorizing Lactobacillus strains from losing their activity, a medium in which growth of the strains are stimulated by addition of F-ingredients thereto as well as a medium containing F-ingredients must be employed for cultivation thereof. The decrease in activity of the deodorizing Lactobacillus strains was observed during the experiments therefor. Moreover, since such phenomenon was also observed during the subculture and storage of said strains, it became of great importance to seek conditions for subculturing the strains while keeping their strong activity. Therefore, in view of the fact that the deodorizing Lactobacillus strains sometimes increase their activity by subculturing them in low nutritional media containing F-ingredients and that they decrease their activity rapidly by subculturing in high nutritional media, the inventor carried out experiments by using the basic low nutritional media containing or not containing S.N.C-compounds, i.e., the odoriferous ingredients of excrements classified by the inventor. Table 10 shows typical and illustrative examples of such experiments.

TABLE 10

| Compounds added to the basic medium | 3rd- | 6th-generations | 9th- |
|---|---|---|---|
| 0.5 g of Na₂S + 0.5 g of NH₃ + 1 g of acetic acid | ◉ | ◉ | ◉ |
| 1 g of acetic acid | ◉~O | O | O |
| 5 g of skim milk | O~ | O~ x | x |

Further, while in the above-mentioned experiments Na₂S, NH₃ and acetic acid were employed representatively as the compounds which serve to maintain the activity of the strains, it was simultaneously made clear that any one of compounds designated as S.N.C-compounds by the inventor such as methyl sulfide, mercaptan, skatole, indole, butyric acid and propionic acid can in all of the cases give almost the same results as above insofar as they are used in combination of said S.N.C-compounds. Then, the changes in the deodorizing activity of the strains which were estimated by adding various amino acids and proteins to the basic medium are shown in the following Table 11.

TABLE 11(A)

| | Compounds added to the basic medium (i.e., S-W + vitamins) | Results of subculture | | |
|---|---|---|---|---|
| | | 3rd- | 6th-generations | 9th- |
| Protein | Peptone | x | * | * |
| Peptide | Meat extracts | x | * | * |
| | Skim milk | x | * | * |
| Amino acids | Cystine | ◉ | ◉ | ◉ |
| | Cystein | ◉ | O | O |
| | Methionine | ◉ | O | O |
| | Alanine | O | x | * |
| | Phenylalanine | O | x | * |
| | Arginine | O | x | * |
| | Asparagine | O | x | x |
| | Aspartic acid | O | x | x |
| | Glycine | O | x | x |
| | Glutamic acid | ◉ | O | O |
| | Aminobutyric acid | x | x | * |
| | Leucine | x | x | * |
| | Isoleucine | x | x | * |
| | Histidine | x | x | x |
| | Proline | x | * | * |
| | Lysine | ◉ | O | x |
| | Tyrosine | x | x | * |
| | Tryptophan | x | * | * |
| | Threonine | x | * | * |
| | Serine | x | * | * |

Note:
◉: No decrease in activity
O: Slight decrease in activity
◯ : Moderate decrease in activity
x: Decrease in activity
*: Remarkable decrease in activity (S-W) refers to the Stephenson-Whetham medium. As is clear from Table 11(A), the specific four to five amino acids were effective to maintain the activity of the strains during the subculture thereof. On the contrary, other amino acids such as proline and tyrosine served to decrease the deodorizing activity of the strains rapidly. That is, it was first confirmed by this experiment that amino acids are mainly divided into three groups: the first group of amino acids which serve to maintain the activity of the deodorizing Lactobacillus strains; the second group of amino acids such as glycine, glutamic acid and lysine which induce a slight decrease in the activity of the strains; and the third group which induce remarkable decrease in said activity. Thus, although it was observed heretofore that the deodorizing Lactobacillus strains decrease their activity when cultivated in a good nutritional medium, the inventor could succeeded in solving such problem on the basis of the above-mentioned finding.

Moreover, the above-mentioned experiments were also meaningful in that some compounds other than the odoriferous ingredients of excrements such as the S.N.C-compounds have been found to serve to maintain the activity of the strains during the subculture thereof. Additionally, it was found that even a single compound may be effective to maintain the activity of the Lactobacillus of the invention insofar as said compound contains S.N.C. This finding may become of great importance from a practical point of view.

Further, as shown in Table 11(B), good results may also be obtained by the use of a mixture of S.N.C.-compounds and specific amino acids.

TABLE 11(B)

| S.N.C-compounds | Amino acids added to S.N.C-compounds | Results of subculture | | |
|---|---|---|---|---|
| | | 3rd- | 6th- | 9th- |
| | | | generations | |
| 0.2 g of Na₂S + 0.2 g of NH₃ + 0.4 g of acetic acid | Cystine | ◉ | ◉ | ◉ |
| | Cystein | ◉ | ◉ | ◉ |
| | Methionine | ◉ | ◉ | ◉ |
| | Glycine | ◉ | ◉ | ○ |
| | Glutamic acid | ◉ | ◉ | ○ |
| | Asparagine | ◉ | ◉ | ○ |
| | Aspartic acid | ◉ | ◉ | ○ |
| | Lysine | ◉ | ◉ | ○ |
| | Arginine | ◉ | ◉ | ○ |
| | Phenylalanine | ◉ | ◉ | ○ |
| 0.5 g of Na₂S + 0.5 g of NH₃ + 1 g of acetic acid | Casamino acids | ◉ | ○ | ○ |

With respect to methods of storage and pharmaceutical compositions:

Various methods for storage of strains and pharmaceutical compositions containing them have been known. The Lactobacillus strains of the present invention can be stored by various known methods such as refrigeration, dryness, dryness in vacuo or in a liquid form. However, as already been made clear by the inventor's experiments, in storing the strains, special care should sometimes be paid so as to prevent decrease of the deodorizing activity which is a characteristic property of the Lactobacillus strains of the present invention. Namely, when the strains are stored at a low or middle temperature, in a liquid form or by refrigeration or dryness in the presence of a compound which, in subcultiring the strains, serves to decrease the activity thereof, the strains would also decrease their deodorizing activity as in case of the subculture thereof.

Tables 12 and 13 show the results of experiments carried out by the inventor.

TABLE 12

| Compounds added to the basic medium (i.e., S-W + vitamins) | Effects of compounds upon storage of the strains | | | | | |
|---|---|---|---|---|---|---|
| | 28° C. | | | 8° C. | | |
| | dried form | semi-dried form | moistened form | dried form | semi-dried form | moistened form |
| Na₂S | ◉ | ◉ | ◉ | ◉ | ◉ | ◉ |
| Methyl sulfide | ○ | ○ | ○ | ○ | ○ | ○ |
| NH₄Cl | ○ | ○ | ○ | ○ | ○ | ○ |
| Mercaptan | ○ | ○ | ○ | ○ | ○ | ○ |
| Skatole | ○ | ○ | ○ | ○ | ○ | ○ |
| Indole | ○ | ○ | ○ | ○ | ○ | ○ |
| Sodium acetate | ◉ | ◉ | ◉ | ◉ | ◉ | ◉ |
| Sodium butyrate | ◉ | ◉ | ◉ | ◉ | ◉ | ◉ |
| Sodium propionate | ○ | ○ | ○ | ○ | ○ | ○ |

Note:
(S-W): Same as defined hereinbefore

Table 12 shows the result of experiments which were carried out in the presence of a suitable amount of either one of S.N.C-compounds, and this result demonstrates that said compounds are effective to maintain the deodorizing activity of the strains.

TABLE 13

| Compounds added to the basic medium (i.e., S-W + vitamins) | | Effects of compounds upon storage of the strains | | | | | |
|---|---|---|---|---|---|---|---|
| | | 28° C. | | | 8° C. | | |
| | | dried form | semi-dried form | moistened form | dried form | semi-dried form | moistened form |
| Protein + Peptide | Peptone | * | * | * | * | * | * |
| | Meat extracts | * | * | * | * | * | * |
| Amino acids | Skim milk | x | x | x | x | x | x |
| | Cystine | ◉ | ◉ | ◉ | ◉ | ◉ | ◉ |
| | Cystein | ○ | ○ | ○ | ○ | ○ | ○ |
| | Methionine | ○ | ○ | ○ | ◉ | ○ | ○ |
| | Alanine | x | x | x | x | x | x |
| | Phenylalanine | x | x | x | x | x | x |
| | Arginine | ○ | x | x | ○ | ○ | x |
| | Asparagine | x | x | x | x | x | x |
| | Glycine | ○ | x | x | ○ | x | x |
| | Glutamic acid | ○ | ○ | x | ○ | ○ | x |
| | Aminobutyric acid | x | x | x | x | x | x |
| | Leucine | x | x | x | x | x | x |
| | Isoleucine | x | x | x | x | x | x |
| | Histidine | ○ | x | x | ○ | x | x |
| | Proline | x | x | x | x | x | x |
| | Lysine | ○ | ○ | x | ○ | ○ | x |
| | Tyrosine | x | x | x | x | x | x |
| | Tryptophan | x | x | x | x | x | x |
| | Threonine | x | x | x | x | x | x |
| | Serine | x | x | x | x | x | x |

Note:
Dried form: water content = about 8%
Semi-dried form: water content = about 15%
Moistened form: a fermentation broth of the strain, or a mass of living cells of the strain. The strains stored under dried conditions keep their deodorizing activity for a longer period of time as compared with those stored under moistened conditions.

Concomitantly, when stored by lyophilization or at an extremely low temperature, even the strains coated with milk do not lose their deodorizing activity but are kept in good condition. Also in such cases, however, it is preferred to coat the strains with sulfur-containing amino acids.

As in case of the aforementioned subculture thereof, good results can also be obtained under either dried, semi-dried or moistened conditions when the strains are stored in the presence of a mixture of S.N.C-compounds and amino acids.

From Table 13 it has been found that the coating of the strains with amino acids such as cystine or methionine is effective for the storage thereof. This indicates that the strains of the present invention can be administered directly to a living body. This also indicates that various methods other than lyophilization and storage at a low temperature can be employed in making the pharmaceutical compositions of various forms. For example, when the strains are cultivated in a medium containing a large amount of Na₂S, NH₃ and butyric acid and they do not digest said compounds completely, the strains must be washed exhaustively. This washing detracts from the storage conditions of the strains. However, from the above-mentioned facts it is clear that, in such cases, cystine and methionine which have been recognized to be useful for the living body can be employed as the coating agent of the strains.

Various properties of the deodorizing strains of the invention such as the biochemical property and deodorizing activity thereof are shown in the following lines, using the six strains as the representative examples thereof.

Table 14 shows the biochemical properties. On the other hand, the relationship between the nutritional requirements and growth of the strains are shown in Tables 15 and 16. Further, Table 17 shows the effects of the strains upon deodorization of excrements. The experiments of Table 17 was carried out by adding a few loopful of the strains or a fermentation broth thereof to fresh excrements or a 5-fold diluents thereof, and then cultivating the mixture.

TABLE 14

Microscopic observation and morphological characteristics

| | FERM-P Nos. | | | | | |
|---|---|---|---|---|---|---|
| | 1946 | 2742 | 2779 | 2780 | 2781 | 2782 |
| Gram | + | + | + | + | + | + |
| Shape | short rod, rounded ends | cocco-bacilli | short rod, rounded ends | cocco-bacilli | cocco-bacilli | short rod, rounded ends |
| Fragella | − | − | − | − | − | − |
| Capsule | | | | | | |
| Motility | − | − | | − | − | − |
| Cultivation In a medium of (Agar + sugar + vitamins) | anaerobic to microaerophilic round middle colonies | | | | | |
| Projection | semi-spherical, thick | semi-spherical, thick | semi-spherical, average | semi-spherical, thick | thin | semi-spherical, thick |
| Surface Circumference | smooth, moistened plain | | | | | |
| Color | milky white, not transparent, mucous | milky white, not transparent, mucous | milky white, not transparent, mucous | milky white, not transparent, mucous | white, not transparent, mucous | milky white, not transparent, mucous |

TABLE 15

(General properties)

| | FERM-P Nos. | | | | | |
|---|---|---|---|---|---|---|
| | 1946 | 2742 | 2779 | 2780 | 2781 | 2782 |
| Ammonia-production | − | − | − | − | − | − |
| H₂S-production | − | − | − | − | − | − |
| Indole-production | − | − | − | − | − | − |
| Catalase-production | − | − | − | − | − | − |
| Pigment-production | − | − | − | − | − | − |
| Gelatin-liquefaction | − | − | − | − | − | − |
| Utilization of citric acid | − | − | − | − | − | − |
| Decomposition of urea | − | − | − | − | − | − |
| M.R. reaction | + | + | + | + | + | + |
| V.P. reaction | − | − | − | − | − | − |
| Reduction of nitrates | − | − | − | − | − | − |

TABLE 16

(Ability to decompose sugars)

| | FERM-P Nos. | | | | | |
|---|---|---|---|---|---|---|
| | 1946 | 2742 | 2779 | 2780 | 2781 | 2782 |
| Ribose | − | + | + | + | + | + |
| Galactose | + | + | + | + | + | + |
| Sucrose | + | + | + | + | + | + |
| Maltose | + | + | + | + | + | + |
| Celobiose | + | + | + | + | + | + |
| Lactose | + | + | + | + | + | + |
| Melebiose | + | + | + | + | + | + |
| Raffinose | − | + | − | − | − | − |
| Melezitose | − | + | − | − | − | − |
| Mannitol | − | − | − | − | − | − |

TABLE 17-1

Deodorization of animal's excrements (directly applied to the excrements)

| | | Fresh excrements Total weight: 2 g (%) | Control (no strain was added) | Strains added to excrements: mass of living cells (3 loopful) Period of cultivation after addition | | |
|---|---|---|---|---|---|---|
| Strains | Animals | | | 24 | 48 | 72 |
| | dogs | 100 | 4 | 2' | 2 | 1' |
| | | 20 | 4 | 2' | 1 | 1' |
| 1940 | cows | 100 | 4 | 1' | 1' | 1' |
| | | 20 | 4 | 1' | 1 | 1' |
| | pigs | 100 | 4 | 2 | 2 | 1' |
| | | 20 | 4 | 2 | 2 | 1' |
| | hens | 100 | 4 | 2 | 2 | 1' |
| | | 20 | 4 | 2 | 2 | 1' |
| | humans | 100 | 4 | 2' | 2 | 1' |
| | | 20 | 4 | 2' | 2 | 1' |
| | dogs | 100 | 4 | 3 | 2' | 2 |
| | | 20 | 4 | 3 | 3 | 2' |
| | cows | 100 | 4 | 2 | 1' | 1' |
| | | 20 | 4 | 2 | 1' | 1' |
| 2742 | pigs | 100 | 4 | 3 | 3 | 2' |
| | | 20 | 4 | 3 | 3 | 2' |
| | hens | 100 | 4 | 3 | 3 | 2' |
| | | 20 | 4 | 3 | 3 | 2' |
| | humans | 100 | 4 | 3 | 2' | 2 |
| | | 20 | 4 | 3 | 3 | 2 |
| | dogs | 100 | 4 | 3 | 2' | 2 |
| | | 20 | 4 | 3 | 3. | 2' |
| | cows | 100 | 4 | 2 | 1' | 1' |
| | | 20 | 4 | 2 | 1' | 1' |
| 2779 | pigs | 100 | 4 | 3 | 3 | 2 |
| | | 20 | 4 | 3 | 3 | 2 |
| | hens | 100 | 4 | 3 | 3 | 2 |
| | | 20 | 4 | 3 | 3 | 2 |
| | humans | 100 | 4 | 3 | 2' | 2 |
| | | 20 | 4 | 3 | 3 | 3 |
| | dogs | 100 | 4 | 2' | 2 | 1' |
| | | 20 | 4 | 2' | 2 | 1' |
| | cows | 100 | 4 | 2 | 1' | 1' |
| | | 20 | 4 | 2 | 1' | 1 |
| 2780 | pigs | 100 | 4 | 2' | 2 | 1' |
| | | 20 | 4 | 2' | 2 | 1' |
| | hens | 100 | 4 | 2' | 2 | 1' |
| | | 20 | 4 | 2' | 2 | 1' |
| | humans | 100 | 4 | 2' | 2 | 1' |
| | | 20 | 4 | 2' | 2 | 1' |

TABLE 17-1-continued

Deodorization of animal's excrements (directly applied to the excrements)

| Strains | Animals | Fresh excrements Total weight: 2 g (%) | Control (no strain was added) | Strains added to excrements: mass of living cells (3 loopful) Period of cultivation after addition | | |
|---|---|---|---|---|---|---|
| | | | | 24 | 48 | 72 |
| | dogs | 100 | 4 | 3 | 2' | 2 |
| | | 20 | 4 | 3 | 2' | 2 |
| | cows | 100 | 4 | 2 | 2 | 2 |
| | | 20 | 4 | 2' | 2' | 2 |
| 2781 | pigs | 100 | 4 | 3 | 3 | 2 |
| | | 20 | 4 | 3 | 3 | 2 |
| | hens | 100 | 4 | 3 | 3 | 2 |
| | | 20 | 4 | 3 | 3 | 2 |
| | humans | 100 | 4 | 3 | 2' | 2 |
| | | 20 | 4 | 2' | 2' | 2 |
| | dogs | 100 | 4 | 2' | 2 | 1' |
| | | 20 | 4 | 2 | 2 | 1' |
| | cows | 100 | 4 | 2 | 2 | 1' |
| | | 20 | 4 | 2 | 1' | 1' |
| 2782 | pigs | 100 | 4 | 3 | 2 | 1' |
| | | 20 | 4 | 2 | 2 | 1' |
| | hens | 100 | 4 | 3 | 2 | 1' |
| | | 20 | 4 | 2 | 2 | 2' |
| | humans | 100 | 4 | 2' | 2' | 2 |
| | | 20 | 4 | 3 | 2' | 2 |

Note:
Excrements (%): 100%:100% of excrements 20%:20% of excrements, 80% of water
Living cells: Three loopful of the strain cultivated on the petri dishes were added to the excrements
Fresh excrements: excrements just discharged

TABLE 17-2

Deodorization of animal's excrements (directly applied to the excrements)

| Strains | Animals | Fresh excrements Total weight: 2 g (%) | Control (no strain was added) | Strains added to excrements: Fermentation broth (5 cc) Period of cultivation after addition | | |
|---|---|---|---|---|---|---|
| | | | | 24 | 48 | 72 |
| | dogs | 100 | 4 | 2 | 2 | 1' |
| | | 20 | 4 | 2 | 1' | 1' |
| | cows | 100 | 4 | 1 | 1' | 1' |
| | | 20 | 4 | 2 | 2 | 1' |
| 1940 | pigs | 100 | 4 | 2' | 2 | 1' |
| | | 20 | 4 | 2' | 2 | 1' |
| | hens | 100 | 4 | 2' | 2 | 1' |
| | | 20 | 4 | 2' | 2 | 1' |
| | humans | 100 | 4 | 2' | 2 | 1' |
| | | 20 | 4 | 2 | 2 | 1' |
| | dogs | 100 | 4 | 3 | 3 | 2' |
| | | 20 | 4 | 3 | 3 | 3 |
| | cows | 100 | 4 | 2 | 1' | 1' |
| | | 20 | 4 | 2 | 2 | 2 |
| 2742 | pigs | 100 | 4 | 2' | 2 | 2 |
| | | 20 | 4 | 2' | 2 | 2 |
| | hens | 100 | 4 | 3' | 3 | 2' |
| | | 20 | 4 | 3' | 3 | 2' |
| | humans | 100 | 4 | 3 | 2' | 2 |
| | | 20 | 4 | 3 | 2' | 2 |
| | dogs | 100 | 4 | 3 | 3 | 2' |
| | | 20 | 4 | 3' | 3 | 3 |
| | cows | 100 | 4 | 2 | 1' | 1 |
| | | 20 | 4 | 2 | 2 | 2 |
| 2779 | pigs | 100 | 4 | 2' | 2 | 2 |
| | | 20 | 4 | 2' | 2 | 2 |
| | hens | 100 | 4 | 3' | 2' | 2 |
| | | 20 | 4 | 3' | 2' | 2' |
| | humans | 100 | 4 | 3 | 2' | 2 |
| | | 20 | 4 | 3 | 2' | 2 |
| | dogs | 100 | 4 | 2' | 2' | 2 |
| | | 20 | 4 | 2' | 2' | 2 |
| | cows | 100 | 4 | 2 | 1' | 1' |
| | | 20 | 4 | 2 | 2 | 1' |

TABLE 17-2-continued

Deodorization of animal's excrements (directly applied to the excrements)

| Strains | Animals | Fresh excrements Total weight: 2 g (%) | Control (no strain was added) | Strains added to excrements: Fermentation broth (5 cc) Period of cultivation after addition | | |
|---|---|---|---|---|---|---|
| | | | | 24 | 48 | 72 |
| 2780 | pigs | 100 | 4 | 2' | 2 | 1' |
| | | 20 | 4 | 2' | 2 | 1' |
| | hens | 100 | 4 | 2' | 2 | 1' |
| | | 20 | 4 | 2 | 2 | 1' |
| | humans | 100 | 4 | 2' | 2 | 2 |
| | | 20 | 4 | 2 | 1' | 1' |
| | dogs | 100 | 4 | 3' | 3 | 2' |
| | | 20 | 4 | 2 | 2 | 2' |
| | cows | 100 | 4 | 2 | 2 | 2 |
| | | 20 | 4 | 2 | 2 | 2 |
| 2781 | pigs | 100 | 4 | 2' | 2 | 1' |
| | | 20 | 4 | 2' | 2 | 2 |
| | hens | 100 | 4 | 2' | 2 | 2 |
| | | 20 | 4 | 3' | 2 | 2' |
| | humans | 100 | 4 | 2' | 2 | 2 |
| | | 20 | 4 | 3 | 2 | 2 |
| | dogs | 100 | 4 | 2 | 1 | 1' |
| | | 20 | 4 | 2 | 2 | 1' |
| | cows | 100 | 4 | 2 | 1' | 1 |
| | | 20 | 4 | 2 | 2 | 1' |
| 2782 | pigs | 100 | 4 | 2' | 2 | 1' |
| | | 20 | 4 | 2' | 2 | 1' |
| | hens | 100 | 4 | 2' | 2 | 1' |
| | | 20 | 4 | 2' | 2 | 2' |
| | humans | 100 | 4 | 2 | 2 | 1' |
| | | 20 | 4 | 2 | 2 | 2 |

Note:
Fermentation broth: the strains were cultivated for 48 hours in test tubes, and 5 ml of the fermentation broth thereof were added to the excrements.

Then, Table 18 shows the effects of the strains upon deodorization of excrements. The experiments were carried out by cultivating the representative six Lactobacillus strains of the present invention in the following medium and administering them orally to various animals and humans. Compositions of the medium employed: $KH_2PO_4$, $MgSO_4 \cdot 7H_2O$, NaCl, $(NH_4)_2HPO_4$, $FeSO_4 \cdot 7H_2O$, starch, $CaCO_3$, casamino acids, yeast extracts, $Na_2S \cdot 9H_2O$, acetic acid, butyric acid, propionic acid, ammonia, indole, scatole, cystine and vitamins. After the strains were cultivated in the medium, the living cells thereof were collected by centrifugation. The strains thus collected were in the form of wet cake mixed with bread or butter, and administered orally at the dose of 0.5 g/kg. The effects upon deodorization of the excrements were estimated from the next day of the administration.

Besides, degree of deodorization is as follows through the present invention, O. no odor; 1. dim odor; 1'. very little odor; 2. little odor is smelled initially, but will fade away sooner; 2'. little odor; 3. the odor is less that of the control group; 4. the odor of excrements per se in the control group.

TABLE 18-1

Deodorizing effects (p.o.)

| | Strains (FERM-P Nos.) | |
|---|---|---|
| Animals | 1946 | 2742 |
| Dogs | The deodorizing effects appeared 2 days after the administration and continued for about 30 days. Thereafter the excrements recovered | The deodorizing effects appeared 2 days after the administration and continued for about 5 days. Thereafter the excrements recovered their peculiar |

TABLE 18-1-continued

| | Deodorizing effects (p.o.) | |
|---|---|---|
| | Strains (FERM-P Nos.) | |
| Animals | 1946 | 2742 |
| | their peculiar odor gradually | odor gradually |
| Pigs | The deodorizing effects appeared 2 days after the administration and continued for about 20 days. Thereafter the excrements recovered their odor in the same manner as above | The deodorizing effects appeared 2 days after the administration and continued for about 3 to 4 days. Thereafter the excrements recovered their odor in the same manner as above. |
| Hens | The deodorizing effects appeared 2 days after the administration and continued for about 15 days. Thereafter the excrements recovered their odor in the same manner as above. | Same as above |
| Humans | The deodorizing effects appeared 2 days after the administration and continued for about 15 days. Thereafter the excrements recovered their odor in the same manner as above. | Same as above |

Note:
dogs: mean value of 50 dogs
pigs: mean value of 20 pigs
hens: mean value of 30 hens
humans: mean value of 30 men

TABLE 18-2

| | Deodorizing effects (p.o.) | |
|---|---|---|
| | Strains (FERM-P Nos.) | |
| Animals | 2779 | 2780 |
| Dogs | The strain showed almost the same effects as those of Strain No. 2742. | The deodorizing effects appeared 2 days after the administration, but said was not strong and disappeared in 7 to 10 days. |
| Pigs | Same as above | Same as above |
| Hens | Same as above | The deodorizing effects appeared 2 days after the administration, but said was not strong and disappeared in about 5 days |
| Humans | Same as above | Same as above |

TABLE 18-3

| | Deodorizing effects (p.o.) | |
|---|---|---|
| | Strains (FERM-P Nos.) | |
| Animal | 2781 | 2782 |
| Dogs | The strain showed almost the deodorizing effects, but the period of deodorization was a little shorter | The strain showed almost the same deodorizing effects for almost the same period as those of Strain No. 2779. |
| Pigs | Same as above | Same as above |
| Hens | Same as above | Same as above |
| Humans | Same as above | Same as above |

From the above-mentioned biological properties and nutritional requirements thereof it is clear that the Lactobacillus strains of the present invention, except for the properties common to the genus Lactobacillus, differ over a wide range in their properties such as nutritional requirements and the ability to decompose sugars. For example, some strains of the invention may grow in (S-W)medium, and others may show a good growth in (S-W+vitamins)medium. It is generally known that once the technique for isolation of strains is established, it becomes quite easier to isolate many similar strains. Likewise, the inventor has succeeded in isolating many deodorizing Lactobacillus strains. Notwithstanding a fact that various properties of these isolated strains were examined, however, only the strains which differ in their properties have been described in the present invention by omitting the similar ones. Nevertheless, the Lactobacillus strains of the present invention isolated by the inventor, as has been made clear and as explained in length in the present invention, have the common properties of biologically fundamental importance. Such common properties are the remarkably lower nutritional requirements and faster growth rate as compared with the known Lactobacillus strains, the final yields, the peculiar sensibility to S.N.C-compounds and such reactions to various amino acids as not observed in the known Lactobacillus strains. Thus, the present invention is very significant in that the strains which are individually different in their properties have been found to have extremely important common features as far as they are observed from the viewpoint of their deodorizing activity. Accordingly, with respect to the strains having these common properties, the inventor has herein designated them as "the deodorizing lactobacillus strains".

The investigations as to Lactobacillus strains themselves have the longest history in the history of bacteriology, and said investigations have been continued both in the western and eastern countries. Therefore, it would seem possible that the strains which grow in low nutritional media have been isolated independently of the inventor's investigations(though publications reporting such strains have not been found by the inventor's searches). In any case, however, the inventor is the first to have made clear the relationship between the peculiar properties of the strains and the deodorizing effects thereof by focusing on said properties of the strains, and there has not yet been known any report or investigation in this respect.

What we claim is:

1. A deodorizing composition comprising (1) the living cells of a Lactobacillus strain whose growth in enabled or promoted in a culture medium comprising at least one medium selected from the group consisting of S-W medium, S-W medium containing vitamins and S-W medium containing casamino acid, said S-W medium being composed of 1 g of $KH_2PO_4$, 0.7 g of $MgSO_4.7H_2O$, 1 g of NaCl, 4 g of $(NH_4)_2HPO_4$, 0.03 g of $FeSO_4.7H_2O$, and 5 g of glucose per 1 liter of water, said culture medium further containing at least one substance selected from the group consisting of hydrogen sulphide, sodium sulphide, ammonia, a lower fatty acid and a sulfur-containing amino acid, and (2) a coating substance comprising sulphur-containing amino acids coated on said cells, said cells having been recovered from a culture medium and then coated with said coating substance, said coating substance being present in an amount sufficient to maintain the deodorizing activity of said cells.

2. The deodorizing composition of claim 1 wherein said strain of Lactobacillus exhibits resistance to antibacterial compounds and condiments.

3. The excrement deodorant composition as claimed in claim 1 wherein said strain of Lactobacillus exhibits antibiotic productivity.

4. The excrement deodorant composition according to claim 1 wherein said anti-bacterial compound is bile.

5. A deodorizing composition of claim 1, wherein said Lactobacillus strain is at least one strain selected from the group consisting of FERM-P Nos. 1946, 2742, 2779, 2780, 2781 and 2782.

6. A deodorizing composition of claim 1, wherein said Lactobacillus strain is one which is obtained by culturing said Lactobacillus strain in a culture medium containing, as a main ingredient, a growth promoting amount or one or more of sulfur-containing amino acids, glycine, glutamic acid, lysine, alanine, phenylalanine, arginine, aspartic acid, hydrogen sulphide, sodium sulphide, ammonia and lower fatty acids, and recovering said Lactobacillus strain.

7. A deodorizing composition of claim 6 wherein said Lactobacillus is recovered by lyophilization.

8. A method of storing a Lactobacillus strain whose growth is enabled or promoted in a culture medium comprising at least one medium selected from the group consisting of S-W medium, S-W medium containing vitamins and S-W medium containing casamino acids, said S-W medium being composed of 1 g of $KH_2PO_4$, 0.7 g of $MgSO_4.7H_2O$, 1 g of NaCl, 4 g of $(NH_4)_2HPO_4$, 0.03 g of $FeSO_4.7H_2O$, and 5 g of glucose per 1 liter of water, and said culture medium further containing at least one substance selected from the group consisting of hydrogen sulphide, sodium sulphide, ammonia, a lower fatty acid and a sulfur-containing amino acid, which comprises recovering said cells from a culture medium, coating said Lactobacillus with sulfur-containing amino acids and then storing said coated Lactobacillus, said sulfur-containing amino acids being present in an amount sufficient to maintain the deodorizing activity of said cells.

9. A method of claim 8, wherein said Lactobacillus strain is at least one strain selected from the group consisting of FERM-P Nos. 1946, 2742, 2779, 2780, 2781 and 2782.

10. A deodorizing composition comprising (1) the living cells of a Lactobacillus strain whose growth is enabled or promoted in a culture medium comprising at least one medium selected from the group consisting of S-W medium, S-W medium containing vitamins and S-W medium containing casamino acid, said S-W medium being composed of 1 g of $KH_2PO_4$, 0.7 of $MgSO_4.7H_2O$, 1 g of NaCl, 4 g of $(NH_4)_2HPO_4$, 0.03 g of $FeSO_4.7H_2O$, and 5 g of glucose per 1 liter of water, and said culture medium further containing at least one substance selected from the group consisting of hydrogen sulphide, sodium sulphide, ammonia, a lower fatty acid and a sulfur-containing amino acid, and (2) at least one coating substance coated on said cells and selected from the group consisting of hydrogen sulphide, sodium sulphide, ammonia and lower fatty acids, said cells having been recovered from a culture medium and then coated with said coating substance, said coating substance being present in an amount sufficient to maintain the deodorizing activity of said cells.

11. A deodorizing composition of claim 10, wherein said Lactobacillus strain is at least one strain selected from the group consisting of FERM-P Nos. 1946, 2742, 2779, 2780, 2781 and 2782.

12. A method of storing a Lactobacillus strain whose growth is enabled or promoted in a culture medium comprising at least one medium selected from the group consisting of S-W medium, S-W medium containing vitamins and S-W medium containing casmino acid, said S-W medium being composed of 1 g of $KH_2PO_4$, 0.7 g of $MgSO_4.7H_2O$, 1 g of NaCl, 4 g of $(NH_4)_2HPO_4$, 0.03 g of $FeSO_4.7H_2O$, and 5 g of glucose per 1 liter of water, and said culture medium further containing at least one substance selected from the group consisting of hydrogen sulphide, sodium sulphide, ammonia, a lower fatty acid and a sulfur-containing amino acid, which comprises recovering said cells from a culture medium, coating said Lactobacillus with at least one substance present in an amount sufficient to maintain the deodorizing activity of said cells and selected from the group consisting of hydrogen sulphide, sodium sulphide, ammonia and lower fatty acids and then storing said coated Lactobacillus.

13. A method of claim 12, wherein said Lactobacillus strain is at least one strain selected from the group consisting of FERM-P Nos. 1946, 2742, 2779, 2780, 2781 and 2782.

* * * * *